United States Patent [19]

Strawder

[11] Patent Number: 5,737,386
[45] Date of Patent: Apr. 7, 1998

[54] COMPUTER FOR AN X-RAY MACHINE

[76] Inventor: Glenn G. Strawder, 3405 Robey Ter., Apt. 302, Silver Spring, Md. 20904

[21] Appl. No.: 657,950

[22] Filed: Jun. 4, 1996

Related U.S. Application Data

[60] Provisional application No. 60/002,247, Jun. 8, 1995.
[51] Int. Cl.$^6$ ............................................. H05G 1/10
[52] U.S. Cl. .................................... 378/95; 378/116
[58] Field of Search .......................... 378/95, 96, 97, 378/108, 109, 110, 111, 112, 116, 117, 118

[56] References Cited

U.S. PATENT DOCUMENTS

| | | | |
|---|---|---|---|
| 4,158,138 | 6/1979 | Hellstrom | 378/116 |
| 4,160,906 | 7/1979 | Daniels et al. | 378/97 |
| 4,403,337 | 9/1983 | Kleinman | 378/95 |
| 4,597,094 | 6/1986 | Kleinman | 378/95 |
| 4,774,720 | 9/1988 | Carbon | 378/116 |
| 4,811,374 | 3/1989 | Kasa et al. | 378/96 |
| 4,819,258 | 4/1989 | Kleinman | 378/111 |

OTHER PUBLICATIONS

Cahoon's Formulating X-Ray Techniques by Thomas T. Thompson, M.D.; Duke University Press (9th Ed. 1979) pp. 148-54 and 180 and 181 no month.

Primary Examiner—David P. Porta
Assistant Examiner—David Vernon Bruce
Attorney, Agent, or Firm—William D. Hall

[57] ABSTRACT

A computer is provided for calculating input data for an X-ray machine which is about to be used for making an X-ray of a body part. The computer has a multiplicity of input devices each dedicated to inputting particular information that should enter into the input information for an X-ray machine including a series of input devices each dedicated to one pathological disease that the body to be X-rayed may have, input devices dedicated to particular body parts, and an input device dedicated to body part thickness. A program causes the computer to compute the input data for the X-ray machine based on the information fed to the computer via the input devices.

11 Claims, 2 Drawing Sheets

COMPUTER FOR AN X-RAY MACHINE

RELATED APPLICATION

This application is a Continuation-In-Part of my prior co-pending Provisional Specification Serial No. 60,002,247, filed Jun. 8, 1995.

BACKGROUND OF THE INVENTION

This invention relates to a device capable of assisting an x-ray technologist with determining the correct x-ray dose to be given to a patient who will have an x-ray taken of a part of his or her body.

Basic Definition of some parameter factors which directly effect the characteristics or intensity of the x-ray beam are: Kilovolts Peak (abbreviation Kv.P)—determines the amount of peak voltage applied to the x-ray tube. Milliamperage (abbreviation MA)—determines the amount of current that flows to the x-ray tube. Time, normally in seconds {abbreviation (s)}—is the length of the period of time the x-rays are emitted.

There are two basic types of operating modes by which an x-ray technologist can operate an x-ray machine.

One of the types of operating modes is called the "Photo-timing Mode". When operating the x-ray machine using this mode, the x-ray technologist does not formulate (calculate) the amount of radiation needed to satisfactorily penetrate the body part being x-rayed and produce a readable x-ray image. In this mode, the x-ray technologist simply presets all of the x-ray exposure parameter factors (Kv.P, MA, and Time) to levels much higher than believed necessary so that the x-ray beam will continue until the photo-cells decide if enough radiation has been used. Once the x-ray exposure is started, the photo-cells located underneath the x-ray table's top surface area begin to receive the x-ray's exiting the body part being x-rayed. When the photo-cells receive a pre-set dosage (amount of radiation) for the particular body part being x-rayed the exposure is then terminated automatically. A major problem when using this mode is that the body part being examined must be perfectly centered over the photo-cells in order to get a satisfactory x-ray image. In general, more than an inch of error in centering of the body part being x-rayed relative to the photo-cells will result in poor image quality. Hence, in the case of such an error there is need to retake the x-ray (re-radiate the patient).

The other type of operating mode is called the "Manual Mode". This is the most commonly used mode as well as the mode closest to the present invention. When using this mode, the x-ray technologist is the one responsible for formulating and calculating the results correctly that determine the dosage (amount of radiation) needed to penetrate a particular body part (with certain elements involved) and produce a satisfactory x-ray image of that particular body part, all from memory and in their minds.

To arrive at the correct amount of radiation to employ when operating the manual mode of the x-ray machine, the x-ray technologist must accurately identify each element found in the pathway of the x-ray beam (from the x-ray tube to the x-ray film). The following is an incomplete list of the elements and parameters that can be found/involved with the pathway of an x-ray beam: Bone, fluids, fat, air, types of x-ray film/cassettes, distances (FFD, OFD, etc . . . ), pathology (emphysema, gout, bone diseases, etc . . . ). In general, each element requires either more or less radiation to be employed depending on its properties (present state of resistance to x-rays). Any variation in the characteristics of any of the above elements may require adjustments in the mount of radiation needed. Sometimes elements may be added and/or subtracted from the x-ray beams pathway by the technologist; in which case such changes must be taken into account. The x-ray technologist must apply an equation or calculation for the specific changes that have occurred and will effect the image quality of the x-ray. His calculation is usually made in his head without the aid of a calculator. Next, the x-ray technologist sets the results (amount of radiation to deliver) in an x-ray exposure form of Kv.P, MA, and Time and then makes the exposure (takes the x-ray). If the x-ray technologist has failed to identify elements (including their make-up) correctly or if human memory fails to recall the correct equation and/or fails to calculate the results correctly, the image quality of the x-ray will probably be poor requiring that the x-ray to be retaken.

Various types of methods to adjust or compute manual x-ray techniques are not new. Also, U.S. Pat. No. 4,774,720, teaches a method of adjustment of an x-ray device when multiple exposures are made very rapidly thereby avoiding the problem of motion or blur. Also, U.S. Pat. No. 4,819,258, teaches an electronic network that automatically sets a predetermined (fixed mount of) Kv.P to produce the x-ray image. U.S. Pat. No. 4,403,337 teaches an automated setting of x-ray technic factors on the basis of (a) automated determination of the thickness of the patient part to be imaged by a non-contact, sonic ranging system, (b) push button selection for the type of examination, and (c) push button selection for the type of patient physique to provide a system in which a non-contact, automatic sonic measurement is made of the thickness of the patient part to be imaged. This measurement is automatically used together with technician-selected type of examination and the type of patient information for automatic setting of an optimum combination of technic factors. U.S. Pat. No. 4,597,094 teaches a ranging transducer is in the path of the x-ray beam while producing ranging information, but is out of the x-ray beams path for the actual taking of the x-ray. U.S. Pat. No. 4,160,906 teaches a group of buttons related to areas of the body and the x-ray technic for those selectable body parts. Hence, there is pre-programmed technic selection for the body part. Moreover the text published by Duke University Press entitled 'Cahoon's Formulating X-ray Techniques' author Thomas T. Thompson, M.D. (9th Ed. 1979) pages 148–154, describes how an x-ray technologist determines the proper adjustment when a particular factor is changed. Pages 180–181 discuss the age correction factors in regards to changing the Ma.S factor.

SUMMARY OF THE INVENTION

The present invention assists x-ray technologists in creating and/or adjusting manual x-ray exposure techniques faster and more accurately than is customarily accomplished.

In one form, the invention employs a computer located in the console/control panel of an x-ray machine. The computer may have a standard keyboard which allows the operator to enter all types of data (patient's name, exam number, ID numbers etc.) as well as make a selection, and answer questions. The operator may also select the type of operating mode, the different elements involved in this case, the parameter settings etc. through this input means. There is pre-programmed software that contains the correct laws and rules of thumb for each selectable element, factor, and parameter setting, etc. which govern the effects that they have on the intensity (amount of radiation) of the x-ray beam when they are either added to, subtracted from, exchanged for and/or any deviation of from the original group (scenario) of selections. With proper entry by the operator of the data, the computer will compute the correct equation and display the results in an x-ray exposure parameter setting for usage. The display screen helps the operator visualize options, parameter settings, elements, patient data, etc. Also, memory software is capable of storing all input data etc. so the operator may recall special parameter settings with specific elements that will produce an image of a particular patients body part that is x-rayed daily (routinely). Permanent recording may be used to transfer the stored data onto paper, diskettes, etc. for storage and future use. Override capability for the operator provides the option of selecting the desired amount of radiation.

The operator puts into the computer all of the elements he believes will be involved in the making of the x-ray, but prior to the actual taking of the x-ray, circumstances may change causing the operator to either add or subtract certain elements which requires the computer to recalculate the exposure parameters to account for the changes that have been selected.

The invention is capable of calculating and adjusting a particular x-ray exposure parameter setting into several other combinations of exposure settings that will produce a similar image quality of the body part being x-rayed at a different setting of parameters when a need calls to reduce the exposure time to prevent motion or calls for an increase/decease in the x-rays image contrast or detail, etc.

In another form the invention may employ a soft key or finger sensitive touch type key pad for operating the device. In still another form the keyboard and/or the computer may be detachable and portable.

DETAILED DESCRIPTION OF THE INVENTION

Figure 1:
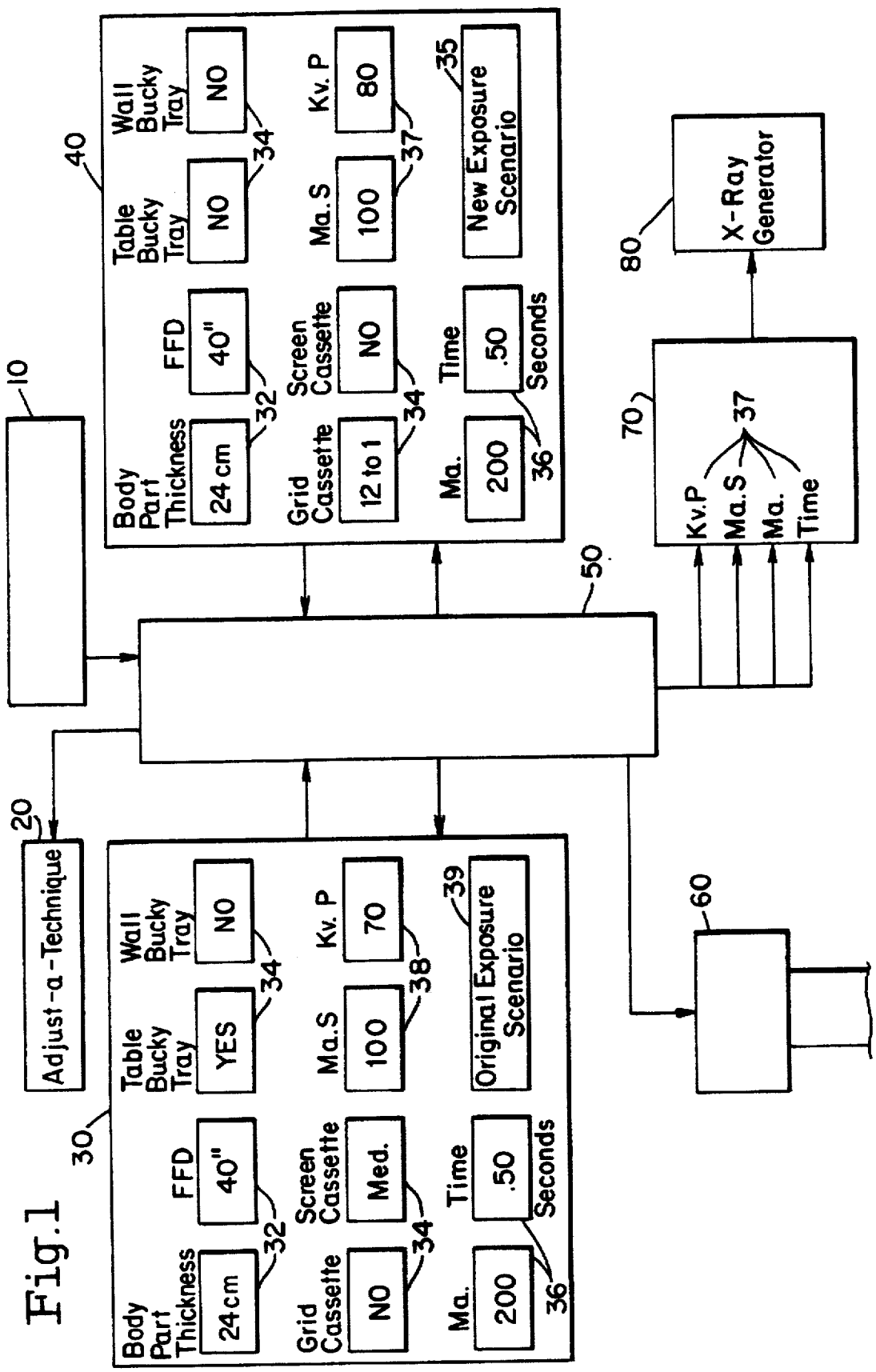
FIG. 1 is a block diagram illustrating an exemplary embodiment of the invention.

FIG. 1 shows a standard typewriter or PC computer keyboard 10 which allows the operator to input data (ie. patient's name, hospital data, exam numbers, date/time, etc.) into the computer 50. There are several types of manual x-ray exposure technique operating modes 20 which the device operates from. Each mode will take various kinds of input data and compute the amount of radiation needed in exposure parameters of Kv.P, Ma.S and/or Distance (FFD). One operating mode allows the operator to create a new manual x-ray exposure technique when the operator does not know what parameter settings (how much Kv.P, Ma.S and/or Distance-FFD) to employ for a particular body part. Another type of operating mode allows the operator to change a desired manual x-ray exposure parameter setting into a new x-ray exposure setting when at least one of the elements 34, factors 32, etc. taken into account when formulating the original exposure settings have now been changed or deviated. There may also be another operating mode which allows the operator to adjust a specific x-ray exposure parameter setting that will produce a certain desired image quality of a particular body part into several other different x-ray exposure paratmeter settings that will produce a similar image quality of the same particular body part being x-rayed. These manual x-ray exposure technique modes 20 are selectable through the keyboard 10 and when selected the computer 50 is then set to perform the correct order of steps to produce that specific type of result after the operator answers all of the questions. A display unit 30 may exhibit the particular type of exposure scenario 39 being displayed as well as the various elements 34, factors 32, parameters 36, anatomical disorders 33 and the exposure parameter setting 38 (amount of radiation) chosen for this particular scenario. The display unit 40 may exhibit another type of exposure scenario 35 as well as list all elements involved including any changes. The laws and rules of thumb that govern each element 34, factor 32, and parameter 36, resistance to x-rays are pre-programmed into computer 50 so that when the operator selects (chooses) to add, subtract, exchange and/or vary any element the computer 50 will compute the correct equation and may adjust the exposure parameter settings 37 automatically with the new results or suggest the amount of adjustment needed either in Kv.P, Ma., Time and/or Distance (FFD). The computer 50 may be capable of re-adjusting the results of the computers computations into a variety of x-ray exposure parameter settings that will produce similar image quality when desired by the operator. Once the final x-ray exposure parameter setting 37 is accepted by the operator the exposure may be made.

Figure 2:
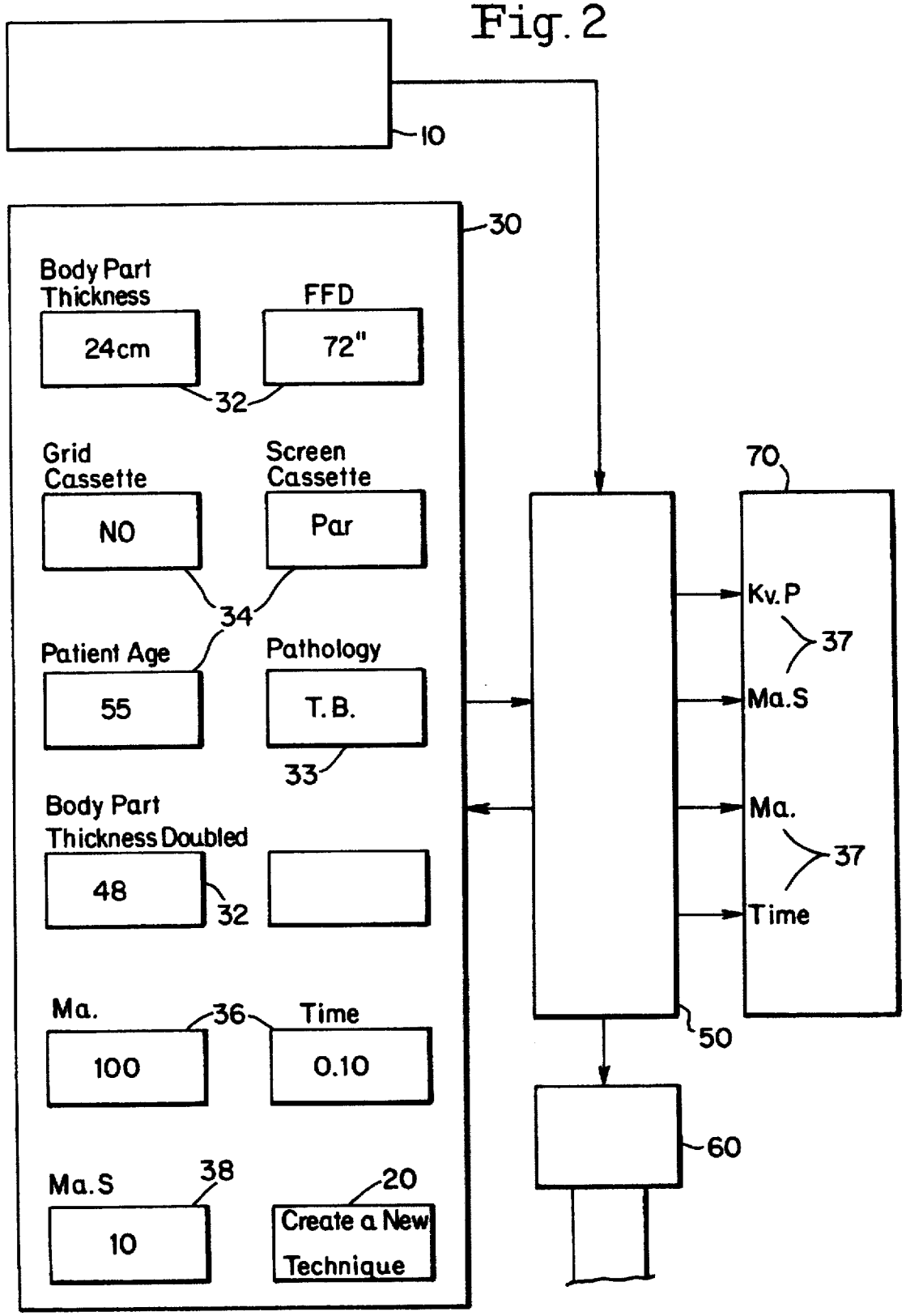
FIG. 2 is a block diagram illustrating an exemplary embodiment of the invention.

FIG. 2 shows another form of the invention with a type of keyboard 10 and display unit 30 with a different type of manual x-ray exposure technique mode 20. Display unit 70 reveals the new x-ray exposure parameter settings 37 that the computer 50 produces as a result of the operator's selections, input data and the computer 50 computations. Printer 60 is a means of providing a permanent record of any data stored by computer 50. Computer 50 may be capable of labeling and storing a special group(scenario) that combines certain elements 34, factors 32 and x-ray exposure parameter settings 37 for specific patient's that have a particular body part x-rayed daily or routinely so that another operator at a later time and date can employ the exact same special group(scenario) of elements 34 etc. with the specific x-ray exposure parameter setting of the amount of Kv.P, Ma.S and/or Distance (FFD) to produce a duplicate of the image quality that was produced earlier of that particular body part for medical comparative reasons. Computer 50 may also be programmed with an x-ray machines individually calibrated body part thickness (BPT) factor 32 so that certain types of manual x-ray exposure techniques can be created by the invention (x-ray machines are calibrated individually therefore each machines BPT factor should differ). Help menu (not illustrated) may be used to guide the operator to select a personal manual x-ray exposure and employ it as opposed to using the computer 50 x-ray exposure parameter settings 37 created from the computation.

For each element that an x-ray technologist will normally take into account in using the invention, there is a dedicated key on the keyboard 10. For example, there is a key dedicated to each type of pathological disease that require an adjustment in the amount of radiation needed such as arthritis, gout, emphysema, Paget's disease, osteoporosis, etc. The x-ray technologist after setting the normal x-ray exposure factors that enter into the calculation of Kv.P, Ma.S and Distance (FFD) to be used for a particular body part, then selects the key for the particular pathological disorder (if any) related to the body part being x-rayed. The computer will apply the correct pre-programmed law/rule of thumb equation for each pathological selection made and display the results in terms of the amount of exposure setting adjustment needed.

In addition to the various keys on keyboard 10 that are dedicated to elements, parameters, factors, etc. that are inputs to the computation, the keyboard 10 has a key that is dedicated to deleting an element, parameter or factor, from the input to the computer. For example, if the operator has inputted a particular parameter, for example, that the patient had gout, the operator may delete gout from the input elements by pressing the delete key followed by the gout key. Once the delete key is pressed the computer 50 will remain in the delete mode until the key dedicated to adding elements is depressed.

Instead of having keys dedicated to deleting and adding elements, there may be codes that place the input of the computer into the delete mode or into the add mode. For example, the code WWW may place the input to the computer into the add mode, and VVV into the delete mode.

Any results (exposure parameter setting) computed by the invention may be re-calculated into a different combination of Kv.P, Ma., Time and/or Distance (FFD) that will result in producing the same or similar image quality of the body part being x-rayed. After the operator has entered information into computer 50, he then may push a mode key which signals the computer to calculate a specific type of manual x-ray exposure technique. Then the operator may enter all the data relating to calculating this specific type of result.

If after the Kv.P, Ma.S, Time and Distance (FFD) have been computed, the operator deems the time to be too long he may press a key dedicated to shortening time. Similarly if he feels that the time is too short he may press a key dedicated to lengthening the time. Next, he inputs the desired percentage of change (for example 40%) of the amount he wishes the time to be either increased or decreased to. Upon selecting the proper key dedicated to increasing or decreasing time and inputting the percentage of change desired the computer then automatically recalculates the Kv.P and/or Ma to give a new set of parameters that will produce the same image quality with the 40% change. Each exposure parameter may be selected for re-calculation in a similar manner as described above.

The x-ray technologist in operating the device will first use keyboard 10 to enter the name etc. of the patient to be x-rayed. The computer 50 will now be advanced to receive the data, elements, parameters etc. that are the input parameters. This may be done automatically (when all preliminary information has been entered) or it may be done by entering a given code, for example ZYX. The computer is now ready for entry of the information on which the calculation (selection of pathological disease) will be based.

In the following paragraph, when I use the word "dedicated", I mean that a key is used for only one function during the entry of input information.

For each parameter, number or other element that goes into the computation of the Kv.P or Ma.S, there is a key on the keyboard 10 dedicated thereto. Thus, if the A key on the keyboard 10 is dedicated to the thickness of the body part to be x-rayed, the thickness of the body part may be entered by pressing the A key followed by entering the number that represents that thickness. In like manner, all other information that is relevant to the calculation may be similarly entered.

The computer 50 will thereafter compute and display the calculated results if the mode key, for any particular formula that the x-ray technologist wishes to use, is pressed. The x-ray technologist may press all the mode keys in sequence to get an answer for each mode.

If a keyboard with less keys than a standard keyboard is used, a combination of letters and/or numbers may represent a given input parameter. For example, the thickness of a body part may be entered with the prefix 3A followed by a number that gives the thickness.

The formulas that are for the above modes that I refer to have a formula that is correct for the x-ray machine in question. In other words, the computer 50 is programmed to provide the correct formulas for the calculations of Kv.P, Ma.S and/or Distance (FFD) for the particular x-ray machine on which the computer 50 is mounted.

Once the above procedure has been followed and the Kv.P and Ma.S calculated for a given x-ray, the x-ray technologist sets the controls on the machine to select the correct input parameters for the machine and then takes the x-ray. Alternatively, the output of the computer could set the inputs to the x-ray machine automatically using known designed techniques.

By way of example, the x-ray technologist (operator) is given a request (doctors order) to x-ray the lower back (lumbar spine) of a patient. The following explains how this would be done with the computer (prior parts). In general, five different x-ray positions (views) are routinely taken for this type of examination. The operator brings the patient into the exam room and has the patient lie on the table face up, which is called the anterior posterior position or AP view. The operator centers the patients lumbar spine region over the midline of the x-ray table. Then the operator positions (centers) the x-ray tube over the patient's lumbar spine region to make sure that the x-ray beams field will cover the body region being x-rayed. Next, the operator places the appropriate sized x-ray cassette/film in the x-ray tables bucky tray located underneath the table top and positions the tray in alignment with the x-ray beam's field and the body region being x-rayed. The operator then goes to the console/control panel area of the x-ray machine where the computer (present invention) is located. In this case the operator does not know the amount of Kv.P and Ma.S to combine that will produce a good x-ray image of this particular body part. The operator first presses the key via keyboard 10 dedicated to selecting the type of manual x-ray exposure technique he wants the computer 50 to create, in this case the 'Create A New Technique' operating mode. The operator next may press the key dedicated to selecting the type of exam (body part) to be x-rayed and the computer 50 then displays the standard amount of Ma.S for that particular body part for this x-ray machine. Each body part may have a standard amount of Ma.S preprogrammed in the computer that will produce a good x-ray image of the standard size for this particular body part when combined with the amount of Kv.P computed. To find the correct amount of Kv.P to combine (employ) with a standard amount of Ma.S for the body part, the operator measures the thickness of the body part being x-rayed (in this case) from front to back with a device called a caliper which measures in inches/centimeters. For example, the body part may measure 24 cm. Next, the operator presses the key dedicated to body parts measurement and then enter 24 into the computer 50 as the parts thickness. The computer 50 then takes that number (24) and for this particular mode of operation automatically doubles the number (24) and gets (24×2=48). The computer 50 then adds this particular x-ray machines BPT factor which is 48 in this example. This gives a total of 88. This number 88 represents the amount or level of kilovoltage (Kv.P) the computer 50 has calculated that should be combined with the standard amount of Ma.S for this particular body part that will produce a good image for the AP view (if no standard amount of Ma.S is pre-programmed in the computer 50 for this particular body part, there may be an operating mode to find a satisfactory amount of Ma.S to employ with the level of 88 Kv.P as calculated above). The operator now may set the control dials of the x-ray machine with the results and take the picture. Afterwards the operator replaces the exposed x-ray film cassette with an unexposed x-ray film cassette and re-positions the patient for the next view which is called the "oblique views".

I will now describe a special situation and then explain how it would be done without the present invention. Assume that the situation calls for the X-ray technologist (operator) to examine (x-ray) the abdomen area of a patient. In this case, the operator goes to where the patient is waiting and reviews the patient's condition, body part size, surveys which elements and factors will be involved, etc. then returns and prepares the x-ray room in the manner he believes the exam will be performed. In this example, the operator prepares the room thinking that certain elements, factors, and parameter setting are going to be used including the x-ray tables bucky grid tray and a medium speed x-ray screen cassette. The operator formulated in his mind how much radiation (exposure parameter setting) it will take to produce a good x-ray image of this patients abdomen using this particular combination of elements and sets the Kv.P and Ma.S control dials to there proper levels and then brings the patient into the room. By the time the patient arrived in the x-ray room the patients condition may have worsened. Now the patient may be weaker and unable to move. The operator may not be able to move the patient from the hospital stretcher onto the x-ray table. At this point, the operator chooses to x-ray the patient while lying on the hospital's stretcher by putting a 12 to 1 stationary grid cassette underneath the patient's body part and realizes that the amount of radiation (Kv.P and/or Ma.S setting) that was to be used for the patient lying on the x-ray table will no longer produce a good x-ray image now that certain element changes have occurred. The operator must now recall spontaneously and accurately the correct laws or rule of thumbs (in this example it would be either the Kv.P grid conversion factors or the Ma.S grid conversion factors) that pertain to the omission of these two elements and the addition of this particular type of grid cassette that will replace the two elements. Then, the operator in his mind must calculate the equations correctly and then use the newly adjusted amount of radiation to take the x-ray with.

The following are the steps that the operator takes when using the present invention instead of his memory to formulate (adjust) the manual x-ray exposure preset in the above prior art example.

Step #1—The operator through the keyboard 10 selects the type of manual x-ray exposure technique to be formulated, in this case the 'adjust-a-technique operating mode' is chosen.

Step #2—The operator inputs via keyboard 10 any important patient data, hospital data, time/date info., etc. that is necessary.

Step #3—The operator at this time has the belief that the patient will be transferred to the x-ray table and presses the keys dedicated to selecting all of the elements including the x-ray tables bucky grid tray and the medium speed x-ray film cassette and any factors or parameter including the x-ray exposure parameter setting believed to be involved in the original group (scenario) selection of elements and acknowledges completion.

Step #4—After the operator has found out that the patient must be x-rayed on the stretcher instead of the x-ray table he then de-presses keys via keyboard 10 dedicated to de-selecting the x-ray tables bucky grid tray and the medium speed x-ray cassette.

Step #5—Next the operator may select (add) the new element (the 12 to 1 stationary grid cassette) that replaces the two elements de-selected in Step #4. In order to add this one element he presses the key on keyboard 10 that is dedicated to adding selected elements and then depresses the key dedicated to the newly added element. Once the selection is made the computer may perform the correct equation(s) governing the exchange.

Step #6—The display unit 70 exhibits the results of the computation performed in x-ray exposure parameter settings of Kv.P, Ma., Time and Distance (FFD) for either the amount of adjustment needed from the original amount suggested and/or the actual exposure settings with the corrected amount of adjustment.

Step #7—Now the operator may choose to either employ the results of the device (invention), or to override to a personal technique setting.

As stated above, one or more keys on the keyboard, or a plurality of codes, are dedicated to selecting the formula used by the computer in making the computation. After all of the input data for computing Kv.P, Ma., and/or Time has been entered, the operator can operate one or more keys to select the particular mode (formula) selected; whereupon the computation is made by the computer. If the operator wishes to do so, the input data for the computer may be entered and thereafter the several modes (formulas) are selected, one at a time, until some or all have been selected and have produced output readings. This procedure gives the operator two or more readings computed by different formulas respectively.

I claim to have invented:

1. A computer for calculating input data for an X-ray machine which is about to be used for making an X-ray of a body, comprising:

a computer having a number of input devices for inputting signals into the computer, said computer comprising means for computing input data for said X-ray machine, a plurality of said input devices comprising means for entering information about the body to be X-rayed, said means for entering information comprising means for entering an identification of the body part to be X-rayed and the thickness of said body part, means for deleting at least some of the input information previously entered, and means for adding new input information to the computer.

2. A computer as defined in claim 1, including means for inputting additional input parameters into said computer which comprises numeric keys for entering numerical data, and keys each dedicated to a particular parameter of input information, for instructing the computer as to the significance of said numerical data.

3. A computer as defined in claim 1 in which said devices comprise the keys of a keyboard.

4. A computer as defined in claim 1, in which said input devices comprise a keyboard having keys, a number of said keys each being dedicated to one type of input information, additional keys comprising numeric keys for entering numerical information that the computer associates with a particular dedicated key.

5. A computer for calculating input data for an X-ray machine which is about to be used for making an X-ray of a body part, comprising:

a computer having means for entering into the computer information to be used in computing the input data for said X-ray machine, said means including a multiplicity of input devices each dedicated to inputting particular information that should enter into the input information for said X-ray machine including (a) series of input devices each dedicated to one pathological disease that the body to be X-rayed may have, (b) input devices dedicated to particular body parts, and (c) an input device dedicated to body part thickness, said computer including program means for computing the input data for said X-ray machine based at least in part on the information fed to the computer via said input devices.

6. A computer as defined in claim 5 in which said input devices include an input device dedicated to deleting information previously entered and an input device for adding new information to replace the deleted information.

7. A computer as defined in claim 5 in which said input data comprises parameters, said computer including an input device for increasing at least one parameter of the computed input data for said machine after the computer has made a calculation of the input data for said machine.

8. A computer as defined in claim 5 in which said input data comprises parameters, said computer including an input device for decreasing at least one parameter of the computed input data for said machine after the computer has made a calculation of the input data for said machine.

9. A computer as defined in claim 5 wherein said computer includes means for inputting into the computer quantities, said input device dedicated to body part thickness including means for entering body part thickness in a quantative form after the input device for body part thickness has been operated.

10. A computer as defined claim 5 in which at least some of said input devices are keys, at least some of said keys are dedicated to a single item of input data.

11. A computer as defined in claim 5 in which at least some of said input devices comprise keys that when two such keys are operated enter one particular item of input data.

* * * * *